United States Patent [19]

Hara

[11] Patent Number: 4,879,387

[45] Date of Patent: Nov. 7, 1989

[54] METHOD FOR MANUFACTURE OF PHTHALIC ANHYDRIDE

[75] Inventor: Tadanori Hara, Kitakyushu, Japan

[73] Assignee: Nippon Steel Chemical Co., Ltd., Tokyo, Japan

[21] Appl. No.: 177,990

[22] Filed: Apr. 5, 1988

[30] Foreign Application Priority Data

Apr. 10, 1987 [JP] Japan ............................. 62-087143

[51] Int. Cl.$^4$ ............................................. C07D 307/89
[52] U.S. Cl. ................................. 549/248; 549/247; 502/218; 502/350; 502/353
[58] Field of Search ................ 549/247, 248; 502/218, 502/344, 353, 350, 352, 309

[56] References Cited

U.S. PATENT DOCUMENTS

| | | | |
|---|---|---|---|
| 3,215,644 | 11/1965 | Kakinoki et al. | 502/218 |
| 3,232,955 | 2/1966 | Nonnenmacher et al. | 502/218 |
| 3,464,930 | 9/1969 | Friedrichsen et al. | 549/248 |
| 3,684,741 | 8/1972 | Friedrichsen et al. | 549/247 |
| 4,036,783 | 7/1977 | Blechschmitt | 549/248 |
| 4,046,780 | 9/1977 | Nakanishi et al. | 549/248 |
| 4,077,984 | 3/1978 | Blechschmitt | 549/248 |
| 4,141,909 | 2/1979 | Wiedemann et al. | 549/248 |
| 4,215,056 | 7/1980 | Schroeder et al. | 549/247 |
| 4,324,694 | 4/1982 | Reuter et al. | 549/248 |
| 4,469,878 | 9/1984 | Kaneyasu et al. | 549/248 |
| 4,472,587 | 9/1984 | Benedetti et al. | 549/248 |

FOREIGN PATENT DOCUMENTS

| | | | |
|---|---|---|---|
| 2546268 | 4/1977 | Fed. Rep. of Germany | 549/248 |
| 3543822 | 6/1987 | Fed. Rep. of Germany | 549/248 |
| 49-34672 | 9/1974 | Japan | 549/248 |
| 52-51337 | 4/1977 | Japan | 549/249 |

*Primary Examiner*—Anthony McFarlane
*Attorney, Agent, or Firm*—Burns, Doane, Swecker & Mathis

[57] ABSTRACT

A method for the manufacture of phthalic anhydride by the catalytic oxidation of naphthlene and/or ortho-xylene which comprises contacting a mixed gas containing naphthalene and/or ortho-xylene and a molecular oxygen-containing gas with a catalyst bed comprising a first catalyst packed on the upstream side of the flow of mixed gas and a second catalyst packed on the downstream side of the flow, wherein the first catalyst has carried on a nonporous inactive carrier a catalytically active component composed of 90 to 67% by weight of titanium dioxide, 8 to 30% by weight of vanadium pentoxide, 2 to 5% by weight of a cesium compound and 0.11 to 0.2 of cesium compound/vanadium pentoxide (molar ratio) (calculated as $Cs_2SO_4$), and the second catalyst has carried on the nonporous inactive carrier a catalytically active component composed of 94 to 67% by weight of titanium dioxide, 5 to 30% by weight of vanadium pentoxide and not more than 0.1% by weight of an alkali metal compound (calculated as sulfate), wherein specific surface are of catalytically active component of first catalyst is at least 20 m$^2$/g.

17 Claims, No Drawings

METHOD FOR MANUFACTURE OF PHTHALIC ANHYDRIDE

BACKGROUND OF THE INVENTION

1. Field of the Invention

This invention relates to a method for the manufacture of phthalic anhydride. More particularly, it relates to a method for producing phthalic anhydride by subjecting naphthalene or ortho-xylene in a gaseous phase to catalytic oxidation with a molecular oxygen-containing gas.

2. Description of the Prior Art

Phthalic anhydride, as widely known, is produced commercially by passing a mixed gas containing naphthalene or ortho-xylene and a molecular oxygen-containing gas at elevated temperatures through a reactor packed with a catalyst thereby causing catalytic oxidation of naphthalene or ortho-xylene. A typical catalyst usable for this method comprises a nonporous inactive carrier and a catalytically active substance comprising 1 to 15% by weight of vanadium pentoxide and 99 to 85% by weight of titanium dioxide deposited in a layer of a thickness of 0.02 to 2 mm on the carrier and used in an amount such that the vanadium pentoxide content falls in the range of 0.05 to 3% by weight based on the catalyst (U.S. Pat. No. 3,464,930). There has been proposed another method which has a phosphorus compound further included in the catalytically active substance deposited on the carrier in the aforementioned catalyst (U.S. Pat. No. 3,684,741).

However, the conventional methods such as described above have proved unsatisfactory in terms of repression of by-products, life of catalyst, yield of phthalic anhydride, etc. These problems become quite conspicuous when naphthalene is used as the raw material. These problems gain in seriousness in proportion as the concentration of naphthalene or ortho-xylene in the feed gas increases. Economically, however, it is desirable that the concentration of naphthalene or ortho-xylene should be so high as to exceed the lower explosive limit. In the meantime, the formation of by-products can be decreased by carrying out the oxidation at as high a temperature, at as low a gas feed volume, and in as low a concentration of naphthalene or ortho-xylene as possible. Under the conditions satisfying all these requirements, however, the productivity of phthalic anhydride is low.

With a view to eliminating the drawbacks mentioned above, there has been proposed a method for effecting the gaseous-phase oxidation of naphthalene or ortho-xylene by using on the up-stream side of the flow of a mixed gas of raw materials a first catalyst carrying thereon a catalytically active substance consisting of vanadium pentoxide and titanium dioxide and containing rubidium in an amount of 0.01 to 0.3% by weight based on the titanium dioxide and containing no phosphorus and on the downstream side of the flow a second catalyst carrying therein a catalytically active substance consisting of vanadium pentoxide and titanium dioxide and containing phosphorus in an amount of 0.02 to 0.8% by weight based on the titanium dioxide and containing no rubidium and a method for gas phase oxidation of naphthalene using a catalyst supporting catalytic ingredients containing 0.1 to 30 mol of titanium dioxide and 0.001 to 0.1 mol of cesium sulfate per 1 mol of vanadium pentoxide as the first catalyst and a catalyst supporting catalytic ingredients containing vanadium pentoxide and titanium dioxide without containing an alkali metal (German Offenlegungsschrift No. P 25 46 268 and Japanese Patent Publication No. sho 49(1974)-34,672).

Even this method has a problem that the yield of phthalic anhydride is not sufficient as a whole. This problem is particularly conspicuous when naphthalene is used as the raw material.

It is, therefore, an object of this invention to provide an improved method for the manufacture of phthalic anhydride.

Another object of this invention is to provide a method for producing phthalic anhydride in high yield and with high productivity (STY).

Still another object of this invention is to provide a method for producing phthalic anhydride from naphthalene as a raw material in high yield and with high productivity.

Further object of this invention is to provide a method for producing phthalic anhydride capable of being selected the oxidation condition such as oxidation reaction temperature range widely.

Yet another object of this invention is to provide a method for producing phthalic anhydride from a mixed raw material of naphthalene and ortho-xylene in high yield and with high productivity.

Yet still another object of this invention is to provide a method for producing phthalic anhydride from any raw materials of naphthalene and ortho-xylene in high yield and with high productivity when any one is changed to the other.

SUMMARY OF THE INVENTION

The objects described above are attained by a method for the manufacture of phthalic anhydride by the catalytic oxidation of at least one raw material selected from the group consisting of naphthalene and ortho-xylene which comprises contacting a mixed gas containing naphthalene or ortho-xylene or both and a molecular oxygen-containing gas with a catalyst bed comprising a first catalyst packed on the upstream side of the flow of mixed gas and a second catalyst packed on the downstream side of the flow, wherein the first catalyst has carried on a nonporous inactive carrier a catalytically active component composed of 90 to 67% by weight of titanium dioxide, 8 to 30% by weight of vanadium pentoxide, 2 to 5% by weight of a cesium compound and 0.11 to 0.2 of cesium compound/vanadium pentoxide (molar ratio) (calculated as $Cs_2SO_4$), wherein specific surface are of the catalytically active component is at least 20 $m^2/g$, and the second catalyst has carried on the nonporous inactive carrier a catalytically active component composed of 94 to 67% by weight of titanium dioxide, 5 to 30% by weight of vanadium pentoxide and not more than 0.1% by weight of an alkali metal compound (calculated as a sulphate), wherein specific surface area of the catalytically active component is at least 5 $m^2/g$.

DESCRIPTION OF THE PREFERRED EMBODIMENT

The first catalyst to be used as packed on the upstream side of the flow of the mixed gas of raw materials in the present invention is formed by having carried on a nonporous inactive carrier 20 to 200 g, preferably 40 to 150 g, per liter of the carrier of a catalytically active component composed of 90 to 67% by weight, preferably 88 to 78% by weight, of titanium dioxide, 8 to 30% by weight, preferably 10 to 20% by weight, of vanadium pentoxide, 2 to 5% by weight, preferably 2.5 to 4.5% by weight, of cesium compound (calculated as $Cs_2SO_4$), provided that the amount of ingredients of the cataliticalloy active component of the first catalyst totals (with the optional ingredient(s) where necessary) 100% by weight. The aforementioned catalytically active component desirably does not contain at least 0.1% by weight of a compound of tin, phosphorus, antimony, bismuth, tungsten and molybdenum. Optionally, it may contains an alkali metal compound such as of K, Rb and the like in small amounts. The specific surface area of the first catalyst is at least 20 $m^2/g$, preferably 40 to 150 $m^2/g$, more preferably 70 to 140 $m^2/g$ as the specific surface area of the catalytically active ingredient, so catalytic activity increases. The specific surface area of the first catalyst may also be 30 to 150 $m^2/g$. The specific surface area can be controlled by selection of titanium dioxide as raw material. For example, the specific surface area may be controlled by using in combination with a commercially available anatase having low specific surface area and titanium dioxide hydrate which can give anatase having high specific surface are by calcination. Further, a method for controlling the specific surface area is described in German Offen legungsschrift No. P 2106796 and the like.

This catalyst may be produced by an ordinary method. For example, it may be produced by dissolving or suspending vanadium pentoxide or any of vanadium compounds such as, for example, ammonium vanadate, and sulfate, oxalate, formate, acetate and tartrate of vanadium which are converted by heating to vanadium pentoxide in water or a mixed solvent of an organic solvent such as alcohol with water, combining the resultant solution with a suitable cesium compound and finely divided titanium dioxide or titanium hydroxide, then, either spraying an inactive carrier with the resultant slurry-like mixture or immersing the inactive carrier in the slurry-like mixture, and heating the carrier with the slurry-like mixture, or spraying the slurry-like mixture on the carrier heated in advance to a stated temperature.

Examples of the cesium compound advantageously usable herein include cesium sulfate, cesium oxide, cesium carbonate, cesium acetate and cesium nitrate. cesium sulfate is preferred to the other cesium compounds cited above. These cesium compounds except cesium sulfate are converted into their corresponding oxides at relatively high temperatures. In the catalyst, cesium exists as cesium sulfate, cesium oxide or cesium vanadate, for example. The most desirable form is the oxyacid salt of sulfur such as cesium sulfate or cesium pyrosulfate.

The second catalyst to be used, as packed on the downstream side of the flow of the mixed gas of raw materials is formed by having carried on a nonporous inactive carrier 20 to 200 g, preferably 40 to 150 g, per liter of the aforementioned carrier of a catalytically active component composed of 94 to 67% by weight, preferably 85 to 70% by weight, of titanium dioxide, and 5 to 30% by weight, preferably 15 to 25% by weight, of vanadium pentoxide. It is preferable that an alkali metal compound such as cesium is contained in the catalytically active ingredients in an amount of not less than 0.1% by weight. However, if a component of phosphorus, tin, antimony, bismuth, tungsten or molybdenum is contained as an oxide in an amount of 0.1 to 3% by weight, the catalytic activity increases. Preferably a phosphorus compound is contained as $P_2O_5$ in an amount of 1 to 2.5% by weight or a tin compound is contained as $SnO_2$ in an amount of 0.2 to 0.6% by weight. Optionally, it may contain compounds of Fe, Co and the like in small amounts. An amount of ingredients of the catalytically active component of the second catalyst totals (with optional ingredient(s) where necessary) 100% by weight.

In the second catalyst the specific surface area is also at least $5 m^2/g$, preferably 30 to 100 $m^2/g$. more preferably 30 to 70 $m^2/g$. The specific area of the first and second catalyst is preferably 30 to 150 $m^2/g$ and 30 to 100 $m^2/g$, respectively.

This catalyst may be produced by an ordinary method, for example. To be specific, it may be produced by dissolving or suspending vanadium pentoxide or any of the aforementioned vanadium compounds capable of being converted by heating into vanadium pentoxides in water or in the aforementioned organic solvent, combining the resultant solution with a suitable tin compound, a suitable phosphorus compound and the like and with finely divided titanium dioxide, then either spraying an inactive carrier with the resultant slurry-like mixture or immersing the inactive carrier in the slurry-like mixture, and heating the carrier wet with the slurry-like mixture, or spraying the slurry-like mixture on the carrier heated in advance to a stated temperature.

When a metal compound such as a tin compound or a phosphorus compound is added, there are oxide, chloride, acetate, etc. of the metal and ammonium phosphate, phosphoric acid, phosphorous acid and phosphoric esters.

The chemical names used in this specification to designate the components for the catalytically active substances are intended solely for the convenience of calculation. As is well known, actually in the catalyst, vanadium is present in the form of $VO_x$ ($x=1$ to 5) or a vanadate and cesium in the form of cesium sulfate or cesium pyrosulfate, for example. By the same token, tin is present in the form of $SnO_x$ or a stannate and phosphorus in the form of $PO_x$ or a phosphate, for example.

Titanium dioxide in the form of anatase, titanium dioxide hydrate, etc. are available as sources for titanium oxide in the catalyst to be used in the present invention.

Examples of the nonporous inactive carrier to be used for the catalyst of the present invention are sintered or fused masses of silicates, steatite, ceramics, alumina and silicon carbide. To be effectively used in this invention, the aforementioned catalyst is desired to be in the shape of spheres, cylinders or rings, for example, which have an equivalent diameter of about 3 to 12 mm, preferably about 6 to 10 mm. The cylinders or rings of the catalyst have a height of about 3 to 10 mm, more desirably about 4 to 8 mm, and most desirably about 70 to 80% of the equivalent diameter. Among other shapes, the shape of rings proves desirable. Particularly the shape of Lessing rings which, as disclosed in Japanese Patent Publication No. SHO 61(1986)-48,980, are a carrier of the shape of tubes each divided into two substantially equal cells by a partition wall disposed substantially perpendicularly to a plane in the diametric direction of the tube, with the tubes each measuring 6 to 10 mm in outside diameter, 4 to 8 mm in inside diameter, and 4 to 10 mm in height, the ratio of the thickness, b mm, of the partition wall to the thickness, a mm, of the peripheral wall of the tube, b/a, falling in the range of 0.4 to 0.8 (providing that b is larger than 0.5), and the thickness of the padding, C mm, of the peripheral wall at the joint between the peripheral wall and the partition wall and the length of the padding, d mm, in the circumferential direction from the intersection between the peripheral wall and the partition wall satisfying the formula, $$C = e \times 0.1 \sim 0.3 - d \times 0.5 \sim 1.5$$

(providing that C is equal to or larger than o and e denotes the inside diameter in mm) proves particularly desirable because it suffers only a little pressure loss and permits oxidation in a high concentration. In the case of the carrier in the shape of rings, the inside diameter of each ring is 2 to 10 mm, preferably about 4 to 8 mm. In the case of the carrier in the shape of Lessing rings, it is proper that the rings should be provided with a partition wall substantially in the center and possessed of a wall thickness of 0.5 to 2 mm, preferably 0.6 to 1 mm.

After the catalytically active substance has been deposited on the carrier, the resultant composite is heated to complete a catalyst. This heating is carried out at a temperature in the range of 300° to 600° C., preferably in an atmosphere of oxygen for a period of 4 to 10 hours to effect required thermal decomposition.

The catalyst completed as described above is used to pack a reactor such as a shell and tube reactor. Then, a mixed gas containing naphthalene or ortho-xylene and a molecular oxygen-containing gas such as air is passed through this reactor to effect catalytic oxidation of naphthalene or ortho-xylene. When the two catalysts are used as described above, the volumetric ratio of the first catalyst to the second catalyst generally is such that the second catalyst has a volume of 30 to 300 parts, preferably 30 to 150 parts, more preferably 30 to 95 parts, based on 100 parts of the first catalyst. The second catalyst may also have a volume of 60 to 150 parts based on 100 parts of the first catalyst. Within the reactor, the second catalyst is packed in a lower layer of a prescribed volume and the first catalyst is packed in an upper layer of a prescribed volume. Downwardly from the upper side of the reactor, the mixed gas consisting of naphthalene or ortho-xylene and a molecular oxygen-containing gas such as air is passed to effect the catalytic oxidation. The reaction temperature (niter temperature) is 300° to 400° C., preferably 330° to 380° C., the concentration of naphthalene or ortho-xylene is 30 to 130 g/m³ of air, preferably 50 to 100 g/m³ of air, and the space velocity of the feed gas is 1,000 to 8,000 hr$^{-1}$, preferably 2,000 to 5,000 hr$^{-1}$. Of course, a mixed raw material of naphthalene and ortho-xylene may be used.

According to the present invention, the first catalyst caused the oxidation with a relatively high selectivity to permit selective conversion of naphthalene or ortho-xylene to phthalic anhydride and the second catalyst effects the oxidation with a high activity and decreases the amount of unreacted hydrocarbon to the fullest possible extent. As a whole, they permit phthalic anhydride to be obtained in a high yield, with the formation of by-produces decreased. The effect of the two catalysts is particularly conspicuous when naphthalene is used as the raw material.

Now this invention will be described more specifically below with reference to working examples. Whenever "%" is mentioned in the following working examples, it is meant to be % by weight unless otherwise specified.

EXAMPLES 1–27

(A) Preparation of First Catalyst

Powdered titanium dioxide (containing anatase type titanium dioxide), ammonium metavanadate and sulfate cesium was added into water and the resultant mixture was thoroughly stirred and emulsified into a slurry liquid. In a rotary furnace, a ceramic carrier of the shape of Lessing rings having 8 mm of outer diameter, 5 mm of inner diameter, 6 mm of height and 1 mm of thickness of partition wall was placed and preheated therein to temperature of 200° to 250° C. Now with the rotary furnace kept in rotation, the preheated carrier was sprayed with the aforementioned slurry liquid so that the carrier would carry 100 g of the catalytically active component per liter of carrier. Under a sweeping flow of air, the resultant composite was calcined at 550° C. for 6 hours to produce a catalyst.

The aforementioned treatments were so , controlled that the catalytically active component of the produced catalyst would be composed of 11 to 15 of $V_2O_5$, 1.0 to 4.0% of $Cs_2SO_4$, and the balance to make up 100% of $TiO_2$. Specific surface area of the catalytically active ingredients is controlled by varying the ratio of two kinds of titanium oxide having different specific surface area. Content of the catalytically active ingredients of the first catalysts in Examples 1–29 and the specific surface area thereof are shown in Table 1.

(B) Preparation of Second Catalyst

Similarly to the first catalyst, powdered titanium dioxide, ammonium metavanadate or further tin chloride, antimony nitrate, bismuth nitrate or ammonium phosphate were added to deionized water. The resultant mixture was stirred and emulsified to produce a catalyst of the form of slurry liquid. By following the procedure used in the preparation of the first catalyst, this liquid catalyst component was sprayed on a carrier of the shape of Lessing rings so that the carrier would carry 80 g of the catalytically active component per liter of carrier. Under a sweeping flow of air, the resultant composite was calcined at 550° C. for 6 hours to produce a catalyst. The treatments mentioned above were so controlled that the catalytically active component of the produced catalyst would be composed of 20% of $V_2O_5$, 0.3 to 2.0% of $SnO_2$, $Sb_2O_3$, $Bi_2O_3$ or $P_2O_5$, and the balance to make up 100% of $TiO_2$. Content % by weight of the ingredients except $TiO_2$ and $V_2O_5$ in the second catalysts in Examples 1–29 and specific surface area of the second catalysts are shown in Table 1.

(C) Production of Phthalic Anhydride

A reaction tube 25 mm in inside diameter immersed in niter bath was packed with a bed of the first catalyst and a bed of the second catalyst downwardly in the order mentioned. A mixed gas of naphthalene and air was passed through this reaction tube. The concentration: naphthalene was 70 g/Nm³, the space velocity was 3,000 hr$^{-1}$, and the temperature of niter was in the optimum range of 340° to 360° C.

The volumetric ratio of the first catalyst to the second catalyst was 110 parts to 100 parts in Examples 1–27. In Example 26, ortho-xylene was used instead of naphthalene and in Example 27, a mixture of naphthalene and ortho-xylene (mixing ratio is 1:1) was used instead of naphthalene. The ratio of the first catalyst- /second catalyst in Example 28 and 29 were 1.5 and 0.8 respectively. Yields of phthalic anhydride and

Controls 1–3

A phthalic anhydride was produced by following the procedure of Examples 1–25, except that the first catalyst bed was prepared with varying an active ingredient of catalyst and a specific surface area as shown in Table 1. The results are shown in Table 1.

Control 4

A phthalic anhydride was produced by following the procedure of Examples 1–25, except that the first and second catalyst bed were prepared with varying an active ingredient of catalyst and a specific surface area as shown in Table 1. The results are shown in Table 1.

Control 5

A phthalic anhydride was produced by following the procedure of Examples 15–22, except that only the first catalyst bed was used. The result is shown Table 1.

rial selected from the group consisting of naphthalene and ortho-xylene which comprises contacting a mixed gas containing naphthalene or orhoxylene or both and a molecular oxygen-containing gas with a catalyst bed comprising a first catalyst packed on the upstream side of the flow of said mixed gas and a second catalyst packed on the downstream side of the flow, wherein the first catalyst is deposited on a nonporous inactive carrier, said first catalyst having a catalytically active component consisting essentially of 90 to 67% by weight of titanium dioxide, 8 to 30% by weight of vanadium pentoxide, 2 to 5% by weight of cesium compound and 0.11 to 0.2 of cesium compound/vanadium pentoxide (molar ratio) (calculated as $Cs_2SO_4$), wherein specific surface area of the catalytically active component is at least 20 $m^2/g$, and the second catalyst is deposited on the nonporous inactive carrier, said catalyst having a catalytically active component composed of 94 to 67% by weight of titanium dioxide, 5 to 30% by weight of vanadium pentoxide and not more than 0.1% by weight of an alkali metal compound (calculated as sulfate), wherein

TABLE 1

| | Active ingredient of first catalyst | | | | Active ingredient of second catalyst | | | | |
|---|---|---|---|---|---|---|---|---|---|
| Example | $V_2O_5$ (%) | $Cs_2SO_4$ (%) | $Cs_2SO_4$ $V_2O_5$ (molar ratio) | Specific surface area ($m^2/g$) | Ingredient except $TiO_2$ | $V_2O_5$ (%) | Specific surface ($m^2/g$) | Yield of phthalic anhydride (wt %) | Yield of naphthoquinone (wt %) | Remarks |
| 1 | 11.0 | 3.0 | 0.136 | 86 | $P_2O_5$ | 2.0 | 41 | 103.1 | 0.31 | |
| 2 | 11.0 | 3.0 | 0.136 | 100 | $P_2O_5$ | 2.0 | 41 | 104.1 | 0.21 | |
| 3 | 11.0 | 3.0 | 0.136 | 116 | $P_2O_5$ | 2.0 | 41 | 104.8 | 0.02 | |
| 4 | 11.0 | 3.5 | 0.159 | 92 | $P_2O_5$ | 2.0 | 41 | 103.3 | 0.42 | |
| 5 | 11.0 | 3.5 | 0.159 | 107 | $P_2O_5$ | 2.0 | 41 | 104.5 | 0.35 | |
| 6 | 11.0 | 3.5 | 0.159 | 138 | $P_2O_5$ | 2.0 | 41 | 105.5 | 0.10 | |
| 7 | 11.0 | 4.0 | 0.181 | 127 | $P_2O_5$ | 2.0 | 41 | 105.5 | 0.12 | |
| 8 | 13.0 | 3.0 | 0.116 | 79 | $P_2O_5$ | 2.0 | 41 | 103.6 | 0.21 | |
| 9 | 13.0 | 3.0 | 0.116 | 93 | $P_2O_5$ | 2.0 | 41 | 104.3 | 0.15 | |
| 10 | 13.0 | 3.0 | 0.116 | 108 | $P_2O_5$ | 2.0 | 41 | 104.8 | 0.05 | |
| 11 | 13.0 | 3.5 | 0.135 | 84 | $P_2O_5$ | 2.0 | 41 | 103.2 | 0.35 | |
| 12 | 13.0 | 3.5 | 0.135 | 99 | $P_2O_5$ | 2.0 | 41 | 104.8 | 0.25 | |
| 13 | 13.0 | 3.5 | 0.135 | 114 | $P_2O_5$ | 2.0 | 41 | 105.1 | 0.21 | |
| 14 | 13.0 | 3.5 | 0.135 | 130 | $P_2O_5$ | 2.0 | 41 | 105.8 | 0.03 | |
| 15 | 13.0 | 4.0 | 0.154 | 88 | $P_2O_5$ | 2.0 | 41 | 103.8 | 0.25 | |
| 16 | 13.0 | 4.0 | 0.154 | 120 | $P_2O_5$ | 2.0 | 41 | 106.0 | 0.15 | |
| 17 | 13.0 | 4.0 | 0.154 | 120 | $SnO_2$ | 0.3 | 62 | 105.0 | 0.01 | |
| 18 | 13.0 | 4.0 | 0.154 | 120 | $SnO_2$ | 0.5 | 55 | 104.7 | trace | |
| 19 | 13.0 | 4.0 | 0.154 | 120 | $Sb_2O_3$ | 0.3 | 63 | 105.2 | 0.03 | |
| 20 | 13.0 | 4.0 | 0.154 | 120 | $S_bO_3$ | 0.5 | 59 | 105.0 | trace | |
| 21 | 13.0 | 4.0 | 0.154 | 120 | $Bi_2O_3$ | 0.5 | 61 | 104.1 | " | |
| 22 | 13.0 | 4.0 | 0.154 | 120 | $Bi_2O_3$ | 0.5 | 56 | 103.8 | " | |
| 23 | 11.0 | 2.5 | 0.113 | 61 | $P_2O_5$ | 2.0 | 41 | 103.5 | 0.38 | |
| 24 | 11.0 | 3.5 | 0.159 | 107 | $P_2O_5$ | 2.0 | 32 | 104.2 | 0.37 | |
| 25 | 11.0 | 3.5 | 0.159 | 107 | $P_2O_5$ | 2.0 | 103 | 104.8 | 0.21 | |
| 26 | 13.0 | 3.0 | 0.116 | 108 | $P_2O_5$ | 2.0 | 41 | 116.2 | — | OX:100% |
| 27 | 11.0 | 3.0 | 0.136 | 116 | $P_2O_5$ | 2.0 | 41 | 110.5 | trace | OX/NA = 1/1 |
| 28 | 13.0 | 3.5 | 0.135 | 130 | $P_2{}_{ll}O_5$ | 2.0 | 41 | 106.1 | 0.32 | volumetric ratio = 1.5 |
| 29 | 13.0 | 3.5 | 0.135 | 130 | $P_2O_5$ | 2.0 | 41 | 104.8 | trace | volumetric ratio = 0.8 |
| Control | | | | | | | | | | |
| 1 | 11.0 | 1.0 | 0.046 | 115 | $P_2O_5$ | 2.0 | 41 | 90.3 | trace | |
| 2 | 13.0 | 1.0 | 0.039 | 103 | $P_2O_5$ | 2.0 | 41 | 92.5 | trace | |
| 3 | 13.0 | 4.0 | 0.154 | 6.5 | $P_2O_5$ | 2.0 | 41 | 91.5 | 5.3 | |
| 4 | 13.0 | 4.0 | 0.154 | 120 | $Cs_2SO_4$ | 4.0 | 42 | 100.5 | 10.2 | |
| 5 | 13.0 | 4.0 | 0.154 | 120 | — | — | 41 | 105.6 | 3.5 | |

OX: Ortho-xylene
NA: Naphthalene

According to the present invention, phthalic anhydride can be obtained from naphthalene or ortho-xylene in high yield under producing low by-product. Further, even if the space velocity and mixing ratio of raw material are high, phthalic anhydride can be obtained in high yield, so productivity is high.

What is claimed is:

1. A method for the manufacture of phthalic anhydride by the catalytic oxidation of at least one raw matespecific surface area of the catalytically active component is at least 5 $m^2/g$.

2. A method according to claim 1, wherein said specific surface area of said first and second catalysts is 30 to 150 $m^2/g$ and 30 to 100 $m^2/g$, respectively.

3. A method according to claim 1, wherein said carrier is in the shape of masses.

4. A method according to claim 3, wherein said masses have an equivalent diameter of about 3 to 12 mm.

5. A method according to claim 3, wherein said masses are in the shape of rings.

6. A method according to claim 5, wherein said rings are Lessing rings have a height of 3 to 10 mm and the height is about 70 to 80% of the equivalent diameter of the rings.

7. A method according to claim 6, wherein said Lessing rings are tubes having an inside diameter of 2 to 10 mm, possessing partition wall substantially in the center of the ring, and having a wall thickness of 0.5 to 2 mm.

8. A method according to claim 1, wherein said reaction is carried out at a temperature of 300° to 400° C. with the concentration of naphthalene or ortho-xylene in the range of 30 to 130 g/m$^3$ of air.

9. A method according to claim 1, wherein the volumetric ratio of the first catalyst to the second catalyst is such that the second catalyst has a volume of 30 to 300 parts based on 100 parts of the first catalyst.

10. A method according to claim 1, wherein the catalytically active component of the first catalyst is consisting essentially of 88 to 77% by weight of titanium dioxide, 10 to 20% by weight of vanadium pentoxide, and 2.5 to 5% by weight of cesium compound (calculated as Cs$_2$SO$_4$) and the catalytically active component of the second catalyst is composed of 70 to 85% by weight of titanium dioxide, 15 to 25% by weight of vanadium pentoxide, 0.1 to 3% by weight of an oxide of at least one element selected from the group consisting of phosphorus, tin, antimony, bismuth, tungsten and molybdenum.

11. A method according to claim 10, wherein said oxide is 1 to 2.5% by weight of a phosphorus compound (calculated as P$_2$O$_5$) or 0.2 to 0.6% by weight of a tin compound (calculated as SnO$_2$).

12. A method according to claim 10, wherein the volumetric ratio of the first catalyst to the second catalyst is such that the second catalyst has a volume of 60 to 150 parts based on 100 parts of the first catalyst.

13. A method according to claim 1, wherein said cesium compound is cesium sulfate.

14. A method according to claim 1, wherein said raw material to be oxidized is naphthalene.

15. A method according to claim 10 wherein the specific surface area of the first catalyst is 70 m$^2$/g to 140 m$^2$/g.

16. A method according to claim 15 wherein the specific surface area of the second catalyst is 30 m$^2$/g to 70 m$^2$/g.

17. A method according to claim 2, wherein said specific surface area of said first catalyst is 40 to 150 m$^2$/g.

* * * * *